United States Patent [19]

Gergely et al.

[11] Patent Number: 5,049,738

[45] Date of Patent: Sep. 17, 1991

[54] LASER-ENHANCED OIL CORRELATION SYSTEM

[75] Inventors: John S. Gergely, Ponca City, Okla.; Roger K. McLimans, Wilmington, Del.

[73] Assignee: Conoco Inc., Ponca City, Okla.

[21] Appl. No.: 484,787

[22] Filed: Feb. 23, 1990

Related U.S. Application Data

[63] Continuation-in-part of Ser. No. 275,232, Nov. 21, 1988, abandoned.

[51] Int. Cl.$^5$ .............................................. G01N 21/64
[52] U.S. Cl. .................................... 250/301; 250/255; 250/459.1; 250/461.1
[58] Field of Search .................. 250/461.1, 459.1, 301, 250/255

[56] References Cited

U.S. PATENT DOCUMENTS

| | | | |
|---|---|---|---|
| 3,899,213 | 8/1975 | Fantasia et al. | 250/301 |
| 4,031,398 | 6/1977 | Callis et al. | 250/458.1 |
| 4,609,821 | 9/1986 | Summers | 250/255 |
| 4,814,614 | 3/1989 | Tsui | 250/301 |

OTHER PUBLICATIONS

Raymond M. Measures, Wayne R. Houston and David G. Stephenson; "Analyzing fluorescence decay." Laser Focus (Nov. 1974) pp. 49–52.
Article entitled "The application of fluid inclusions to migration of oil and diagenesis in petroleum reservoirs", Roger K. McLimans, as published in *Applied Geochemistry*, vol. 2; Nos. 5/6, Sep./Dec. 1987.
Article entitled "Reservoir diagenesis and oil migration: Middle Jurassic Great Oolite Limestone, Wealden Basin"; Southern England, R. K. McLimans and P. E. Videtich; published in *Petroleum Geology of North West Europe*, vol. 1.

*Primary Examiner*—Constantine Hannaher

[57] ABSTRACT

Method and apparatus for precise oil correlation using oil-filled fluid inclusions to form signature plots of fluorescence excitation versus emission versus intensity data. The apparatus uses a tunable light source energized periodically through a given series of wavelengths as directed through a microscope to a fluid inclusion to excite fluorescence. Subsequent fluorescence emission is detected by a monochromator/photomultiplier combination for input to a data acquisition system that processes the data and provides requisite fluorescence output plots indicating more particularly the nature of the fluid inclusion matter, i.e., 3-D fluorescence spectra indicative of the oil. The quality of the oil in terms of API° gravity can also be determined by time-resolution fluorescence spectroscopy to determine fluorescence lifetimes. Finally, program-controlled processing functions to identify and classify selected oil material responses relative to data compiled for a preestablished library of different responses.

14 Claims, 12 Drawing Sheets

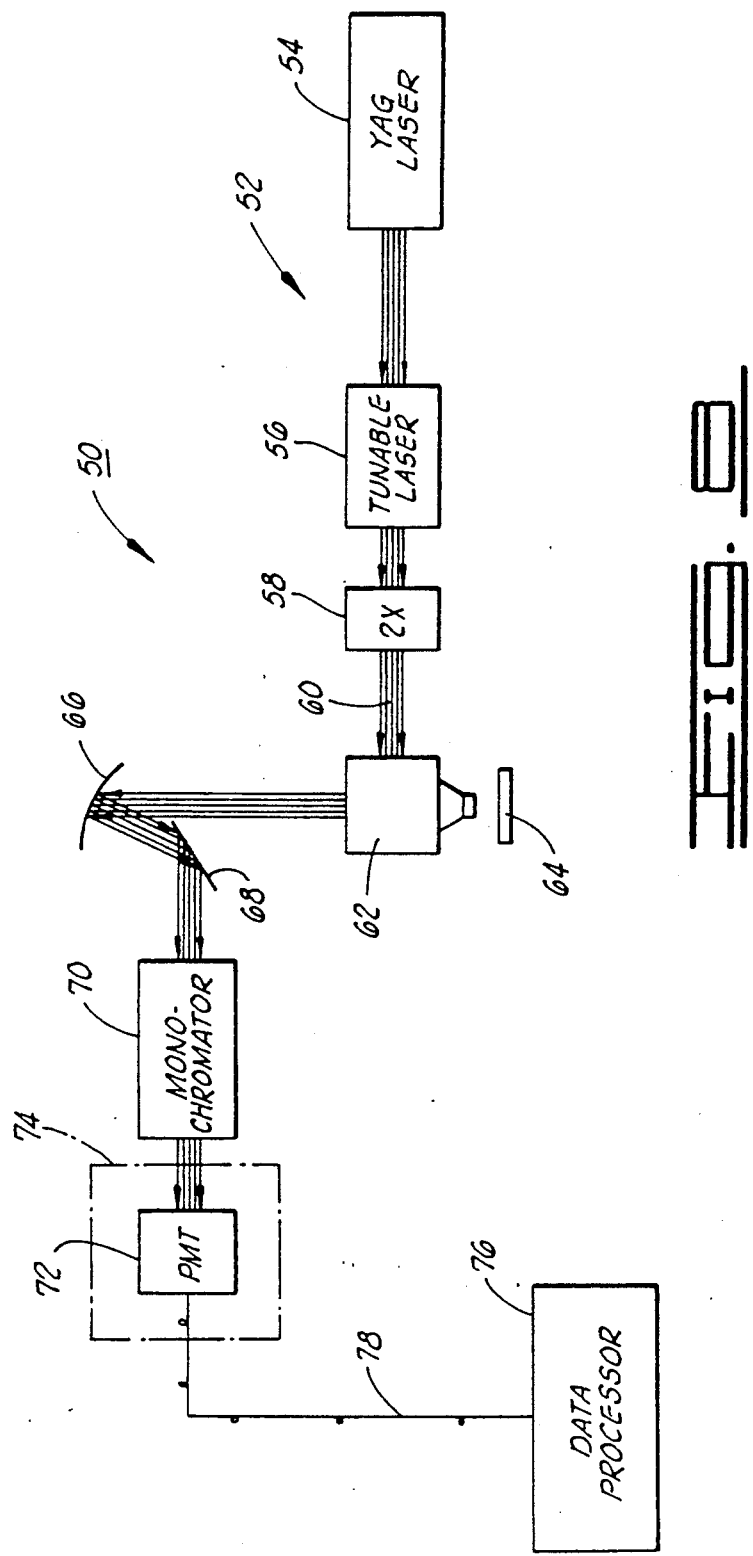

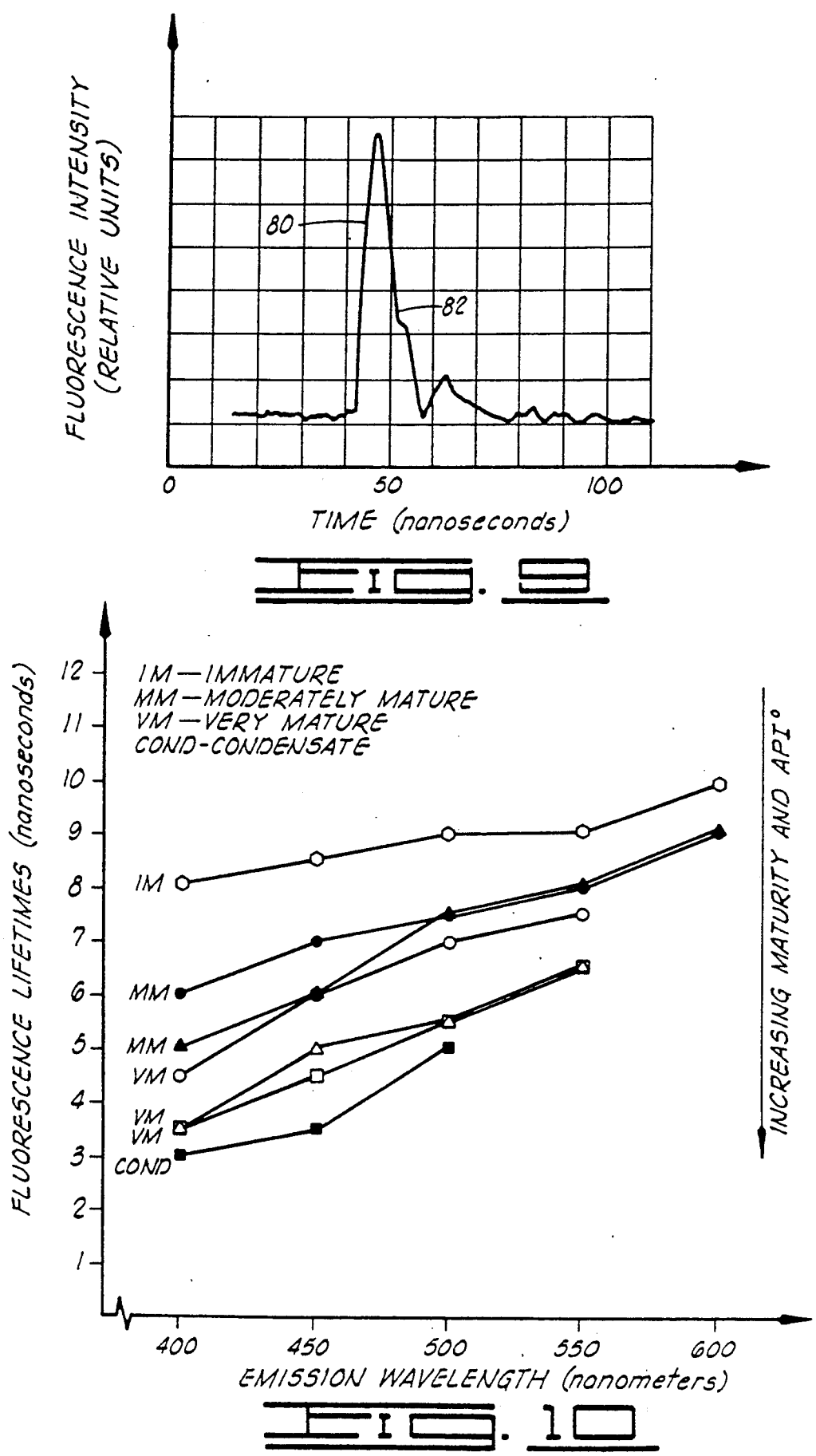

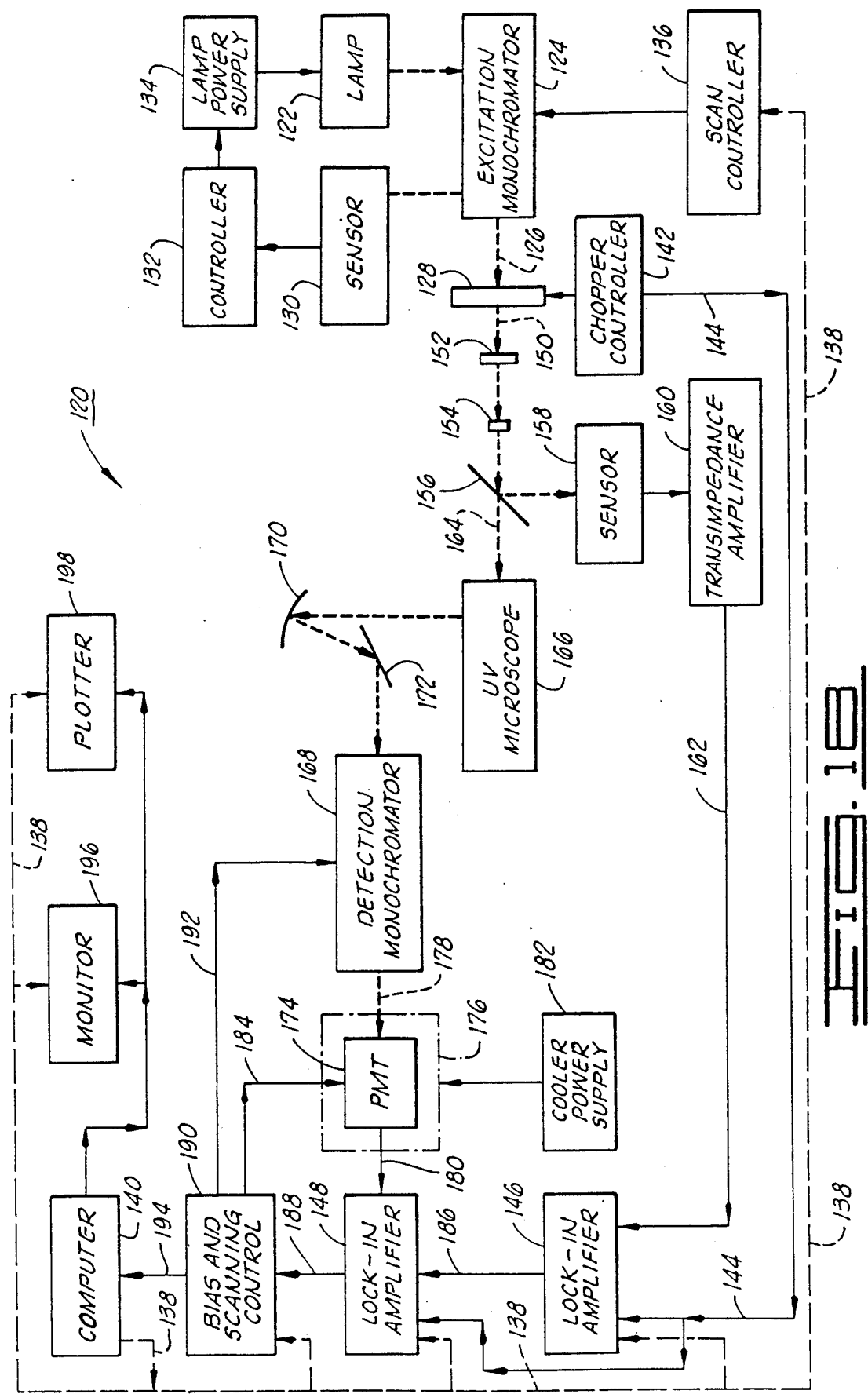

LASER-ENHANCED OIL CORRELATION SYSTEM

CROSS REFERENCE TO RELATED APPLICATION

The present application is a continuation-in-part of U.S. patent application Ser. No. 275,232 filed on Nov. 21, 1988, now abandoned, and entitled "Laser-Enhanced Oil Correlation System".

BACKGROUND OF THE INVENTION

1. Field of the Invention

The invention relates generally to spectrographic identification of petroleum components and, more particularly, but not by way of limitation, it relates to a method of nondestructive examination of fluid inclusions to effect comparisons that better evaluate the petroleum potential of a reservoir, basin or the like to determine presence and migration of particular oil components.

2. Description of the Prior Art

Fluorescence spectrometry per se has been available for a number of years for use in identification of particular materials. An early U.S. Pat. No. 3,899,213 (Fantasia et al.) employed airborne remote sensing using a laser and an associated detector to provide frequency spectrum analysis of a body of water in order to identify oil spills. This device used a telescopically focused scanning laser beam with a narrow band detector and spectrum analyzer for examining any surface fluorescence. The system functioned to develop a distinct fluorescence spectral signature curve which could serve to identify types of oils. U.S. Pat. No. 4,031,398 (Callis et al.) teaches fluorescence spectrometry using television analysis and graphics display which measures in real time all emission and excitation spectra of a sample to provide a complete analysis and signature output of a specific sample. Real time data processing enables display of a graphic format plus recording of the lifetimes of the emitting species.

U.S. Pat. No. 4,616,134 (Pruett et al.) teaches apparatus for high resolution scanning of geologic core samples. This apparatus incites fluorescence of a core geologic sample in line-by-line manner and the emitted radiation is detected and processed digitally to effect analysis as to selected wavelength bands of radiation for the purpose of highlighting and emphasizing framework, composition and texture of the sample. This analysis enables determination of types of oil and other fluids contained in the sample and the relative fluid saturation of the sample.

Finally, U.S. Pat. No. 4,609,821 (Summers) teaches method and apparatus for testing for the presence of native hydrocarbons by examining rock cuttings brought up with drilling mud from a borehole. Samples are prepared by crushing to predetermined consistency whereupon samples are examined with a spectrometer with excitation at one or more wavelengths. Radiation absorbed and/or emitted by the excited sample is sensed and graphic representation is recorded for the excitation and emission wavelengths as against the emission intensity. These parameters enable determination of a characteristic profile for the sample to identify separately the oil-base drilling mud and any native hydrocarbons present within the borehole.

SUMMARY OF THE INVENTION

The invention carries out non-destructive examination of fluid inclusions for comparison of spectral data to other fluid inclusions, crude oils, kerogens, source rock extracts and the like. Such comparison allows evaluation of the petroleum potential of a reservoir or basin, and the possible determination of a migration path of oil when no other existing technique is operable. That is, the present system may be operative when there are no biomarkers available, when oil shows are contaminated by additives to the drilling mud, or when oil-filled fluid inclusions are the only samples available.

The invention consists of the preparation of a very thin slice of earth sample to display the fluid inclusion within a microscope field of view for illumination by a tunable laser or the like. Fluorescence detection and output processing then establishes meaningful output plots of emission wavelength, excitation wavelength and emission intensity to identify the oil substance content of the fluid inclusion.

The invention also contemplates the derivation of fluorescence lifetime measurements to determine the API° of crude oils before a drill stem test. Fluid inclusions, kerogens, drill cuttings, cores and other source rock extracts may be similarly analyzed in non-destructive manner to establish the API° of oil present in relatively small amounts of host material. The fluorescence lifetimes are derived using a pulsed laser excitation and very precise time resolution circuitry or by phase modulation.

A chemometrics computer program has been developed for use in conjunction with 3-D fluorescence spectra of selected oils, inclusions, source rocks or the like as derived from known locations. The program functions to determine API° of the selected oil for subsequent identification and classification relative to a reference data library of 3-D fluorescence spectra for known oils, i.e., oils from known producing areas.

Therefore, it is an object of the present invention to provide a method for fluorescence spectrometry that identifies oil components in situ.

It is also an object of the present invention to establish separately the actual oil components within fluid inclusions in order to better establish hydrocarbon content for a given earth volume.

It is still further an object of the invention to effect non-destructive testing of fluid inclusions to establish distinct signature indications for specific hydrocarbon products as they exist in natural location.

It is another object of the invention to determine the API° from drill cuttings and/or drill cores thereby to obviate a drill stem test.

It is yet another object of the invention to automate procedure for prediction of the API° of a selected oil sample for classification relative to a reference library of fluorescence spectra of known oils.

Finally, it is an object of the present invention to provide a system for microscopically deriving the fluorescence spectra for certain naturally occurring earth deposits to determine geologic history and hydrocarbon make up.

Other objects and advantages of the invention will be evident from the following detailed description when read in conjunction with the accompanying drawings which illustrate the invention.

BRIEF DESCRIPTION OF THE DRAWINGS

FIG. 8 is a block diagram of a fluorescence lifetime measurement system;

FIG. 9 is a graph illustrating a fluorescence lifetime in relative intensity versus time;

FIG. 10 is a graph comparing fluorescence lifetimes for seven oils of diverse maturity;

FIG. 18 is a block diagram of a micro 3-D fluorescence system as evolved for use with the chemometrics API° prediction software.

DETAILED DESCRIPTION OF THE INVENTION

Figure 1:
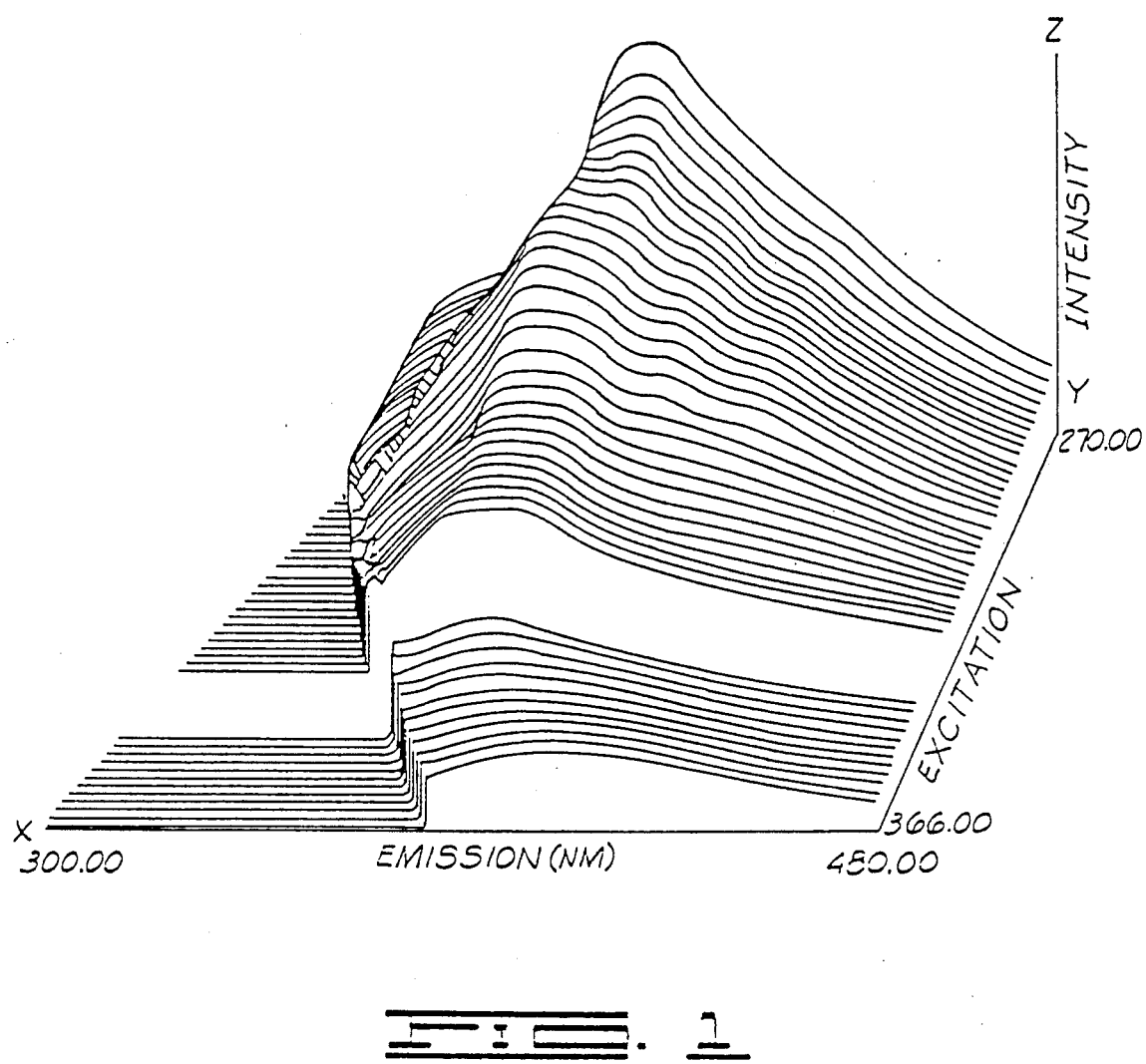
FIG. 1 is a graph representing a three-dimensional fluorescence spectra of a crude oil sample.

FIG. 1 illustrates a 3-D fluorescence spectra of a type that may be obtained using a commercially available fluorescence spectrometer, e.g., the Perkin-Elmer Model LS-4 or MPF66, on a bulk crude oil sample. The vertical or Z axis represents fluorescence emission intensity, the horizontal X axis represents fluorescence emission wavelength, and the orthogonal Y axis represents the fluorescence excitation wavelength emanating from the source irradiating the sample. A spectrometer of this type is not capable of obtaining a 3-D fluorescence spectra from fluid inclusions because of the extremely small size of the inclusion material. The 3-D spectra of FIG. 1 was generated by first illuminating the prepared sample with a selected narrow band wavelength and recording the fluorescence spectrum, e.g., 300 to 480 nanometers. The illuminating wavelength is then moved about 10 nanometers toward the red region, and another fluorescence spectrum is recorded. This is repeated, in this case from 270 to 366 nanometers, until the entire contour as shown in FIG. 1 is obtained and graphically recorded in 3-D format.

In the past, 3-D fluorescence spectra have been obtained from a sample of hydrocarbon product such as crude oil or other ground and prepared earth samples which tend to destroy the information of any individual product constituents as they are mixed in the sample preparation process. Also, if one constituent has strong detection characteristics, it will dominate and suppress characteristics of other constituents into the noise level or render them otherwise unidentifiable.

In order to preserve individuality of information the present invention examines fluid inclusions. It is well known that rocks in the present time contain data related to events that may have occurred millions of years ago. The evidence is meager as to such prehistoric geologic events. Sedimentary rocks undergo a continuum of change from deposition through burial as fluid-rock reactions occur in response to changes in temperature and pressure. The petroleum geologist strives to understand the diagenetic history of potential reservoirs because diagenesis plays a major role in their creation, preservation, and changes in porosity and permeability. Fluid inclusions are store houses of data relating to the temperature, composition and pressure of fluids that invaded a pore system through time. Oil and brine fluid inclusions have been used successfully to determine the timing and physicochemical environments of important events such as cementation, oil migration, and fracturing.

Fluid inclusions are small volumes, i.e., on the order of $10 \times 10^{-10}$ cubic centimeters, of fluid trapped within a crystal. With rare exceptions, such inclusions are the only samples of fluids that were present in the pore systems of rocks in the geological past. During the growth or recrystallization of crystals from a fluid medium, small quantities of that fluid are entrapped as inclusions. Fluid inclusions rarely exceed 1 millimeter in diameter and, generally, the abundance of fluid inclusions is inversely proportional to the inclusion size. The cloudy nature of many cement crystals is due to internal reflections at the interfaces of minute but very numerous fluid inclusions, e.g., $10^9$ per cubic centimeter.

Fluid inclusions form from homogeneous solution and/or heterogeneous mixtures such as oil and water. When the inclusions were formed during the growth of the host crystal, the inclusions are termed "primary". Primary inclusions yield data that is pertinent to the chemical environment of crystal growth. The fluid entrapped as primary inclusions is, therefore, saturated with respect to the components of the host crystal.

Fluid inclusions are also formed in crystals as a result of fluid-rock recrystallization or crystallization of crystals in open space such as fractures. In these cases, the entrapped fluid is a sample of a fluid that entered the pore space at some time, perhaps millions of years, after crystallization of the host crystal was completed. This type of fluid inclusion is termed "secondary".

The distinction between primary and secondary fluid inclusions is critical to data interpretation and is commonly not a simple matter. In the study of petroleum reservoirs, we are generally concerned with primary inclusions as we seek to determine the timing and environments of cement formation. Therefore, a safe working procedure is to consider all fluid inclusions as secondary unless criteria can be demonstrated that indicate a primary origin for fluid inclusions.

Fluid inclusions are observed with the petrographic microscope. Commonly, magnifications of 300 to 500 X are required. In sedimentary rocks, the greatest problem is finding material (generally calcite, dolomite, quartz, or anhydrite as cements) of suitable coarseness. The finer the grain size, the greater the difficulty. Since fluid inclusions are at most a fraction of one percent of the rock volume, the chances of finding suitable inclusions for study diminish rapidly with reduction in grain size. The best samples are cements in medium to coarse grained rocks. Carbonate packstones and grainstones are examples of very good sample material. Quartz sandstones are highly variable in quality for fluid inclusion study because of grain size variations, and because the cements in pores are generally of fine grain size.

Figure 2:
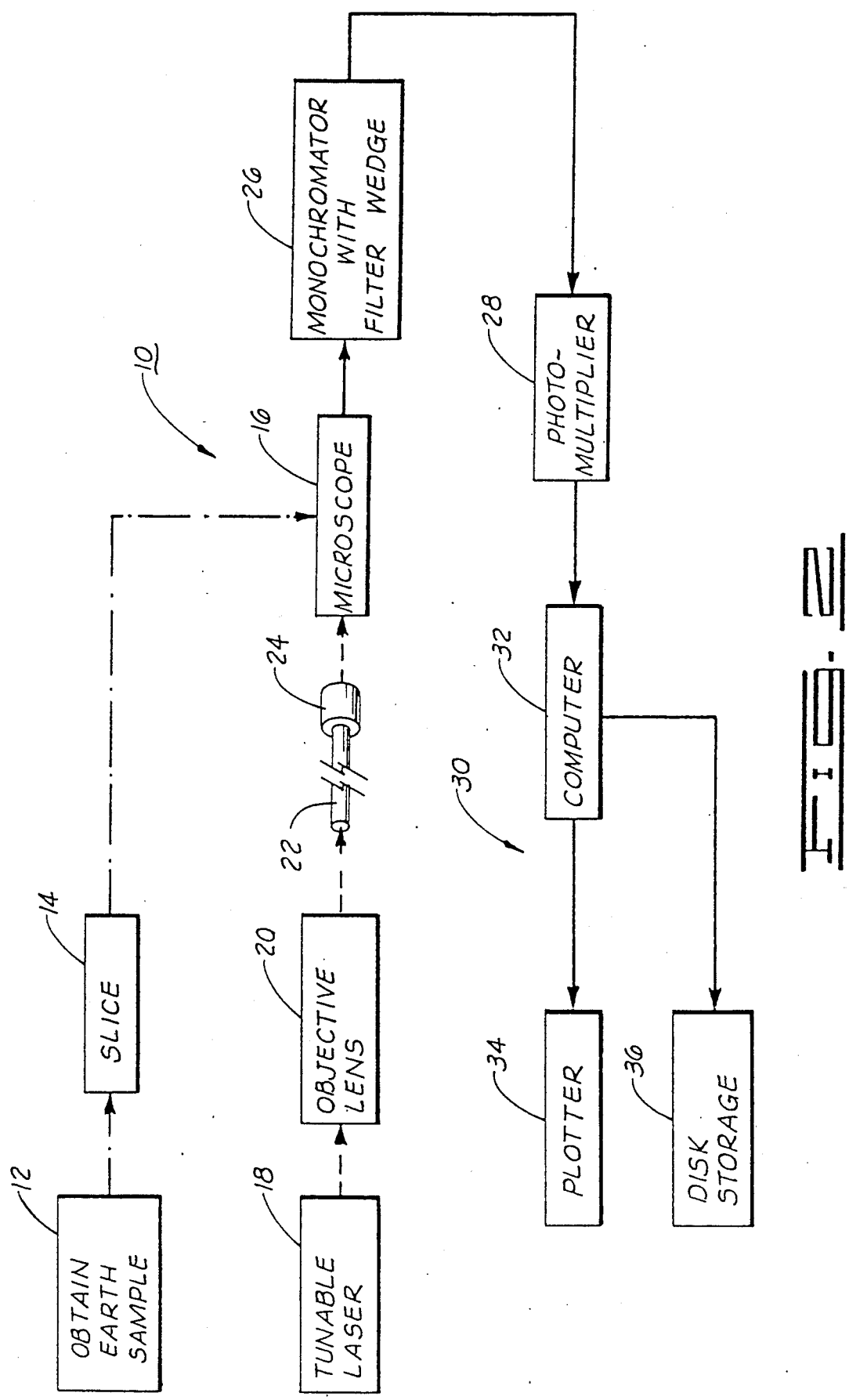
FIG. 2 is a block diagram of apparatus of the present invention.

A sample is prepared by first obtaining a portion of earth from a sector or volume of interest, e.g. part of a drilled core of earth. The sample thus obtained is broken down into lesser parts by cutting so as not to crush the material. A section of the sample providing good fluid inclusion likelihood is then selected for slicing in very thin sections to expose the fluid inclusion crystals. In FIG. 2, the system 10 depicts the step 12 of obtaining the earth sample and the subsequent step 14 of slicing the sample into slices of about 20 microns to 100 microns thickness. Slice thickness is a function of the particular rock type in order to best display the fluid inclusion. A selected slice is then secured on a slide by suitable medium and placed in the viewing target or field of view in a microscope 16. A suitable form of microscope 16 is commercially available from Zeiss Corp. of Thornwood, New York. It should also be understood that prepared kerogen samples and/or smears of oil may be similarly treated for microscopic examination.

Source light is provided by a tunable lamp or tunable laser 18 that provides tunable, narrow band, collimated light with sufficient power to stimulate the 3-D fluorescence spectra from the fluid inclusions in microscope 16. A suitable light source is a tunable argon laser which is available from Cooper Lasersonics of Palo Alto, California. The laser light output is tuned to discrete wavelengths, namely, 454.5, 457.9, 465.8, 472.7, 476.5, 488.0, 496.5, 501.7, and 514.5 nanometers. With additional ultraviolet optics the range can be extended to 351.1 and 363.8 nanometers. More recent work has employed a mode-locked, frequency-doubled YAG laser pumping a tunable dye laser, or a tunable lamp source which provides wide-range, tuning in selected increments. The laser is available from Coherent Radiation, Inc. of Palo Alto, California. The tunable lamp is obtainable from Photon Technology International, Inc. of Princeton, New Jersey.

Laser output from tunable laser 18 is then directed through a lens 20 into a fiber optic cable 22. The output end of fiber cable 22 includes a collimator 24 which functions to facilitate the alignment of the laser light output through the microscope 16. The lens 20, fiber optic cable 22 and collimator 24 may be obtained from Math Associates, Westbury, New York.

Fluorescence emission light from the fluid inclusion in microscope 16 is then detected by a monochromator with filter wedge combination 26 with subsequent light conversion in a photomultiplier tube 28. The monochromator combination 26 scans the light output from the fluid inclusion and photomultiplier 28 converts it to recordable fluorescence spectra data signals which are then input to a data acquisition system 30 for digital conversion and analysis. The monochromator/photomultiplier combination may be obtained from Xeiss Corp. of Thornwood, New York. The data acquisition system 30 consists of a computer 32, data plotter 34 and disc storage 36, and a suitable system is the model Data 6000 as obtained from Analogic Corp., of Peabody Massachusetts.

Figure 3:
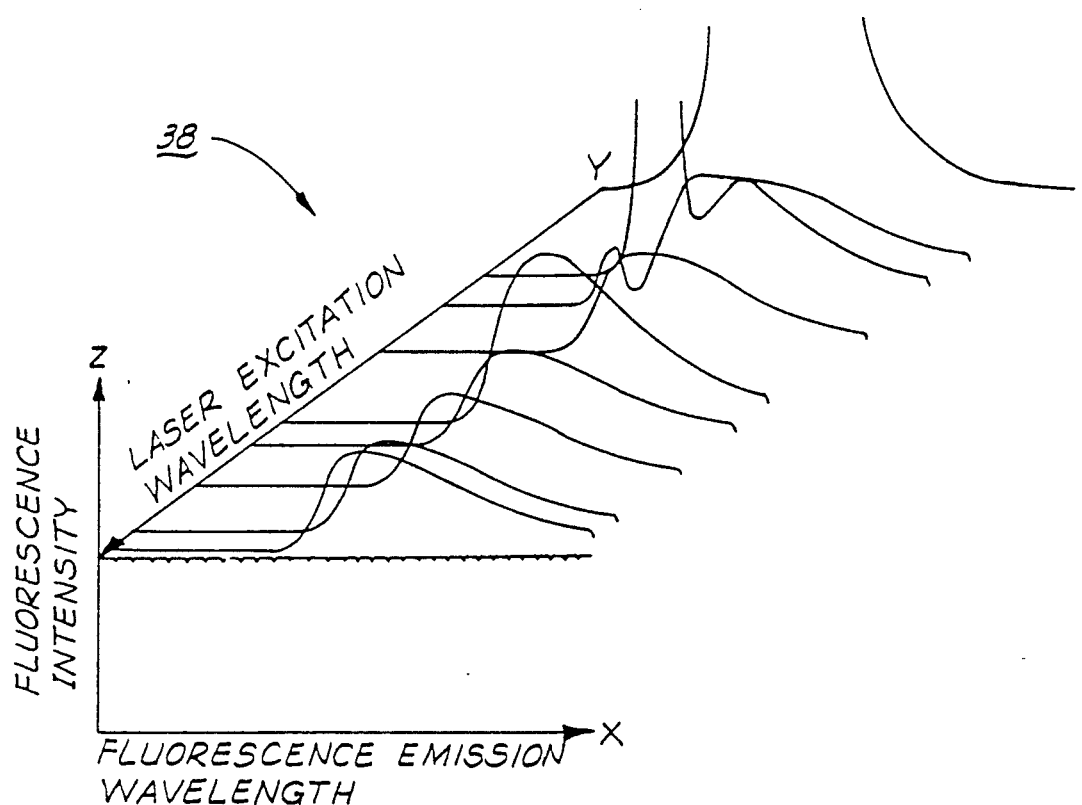
FIG. 3 is a graphic depiction of a three-dimensional spectrum of a selected fluid inclusion as developed by the present invention.

FIGS..3 and 4 illustrate a matchup in a crude oil test for a certain region. FIG. 3 shows the typical 3-D fluorescence plot 38 of an oil-filled inclusion as obtained from a relevant earth site and processed through the laser enhanced correlation system 10. The vertical axis Z represents fluorescence emission intensity, horizontal axis X represents fluorescence emission wavelength, and the orthogonal Y axis represents the laser excitation wavelength. Each of the curves represents the fluorescence emission spectra from the fluid inclusion for a particular laser output or excitation wavelength illuminating the sample. The last two curves of shorter wavelength show laser scatter which may be eliminated by use of proper blocking filter.

Figure 4:
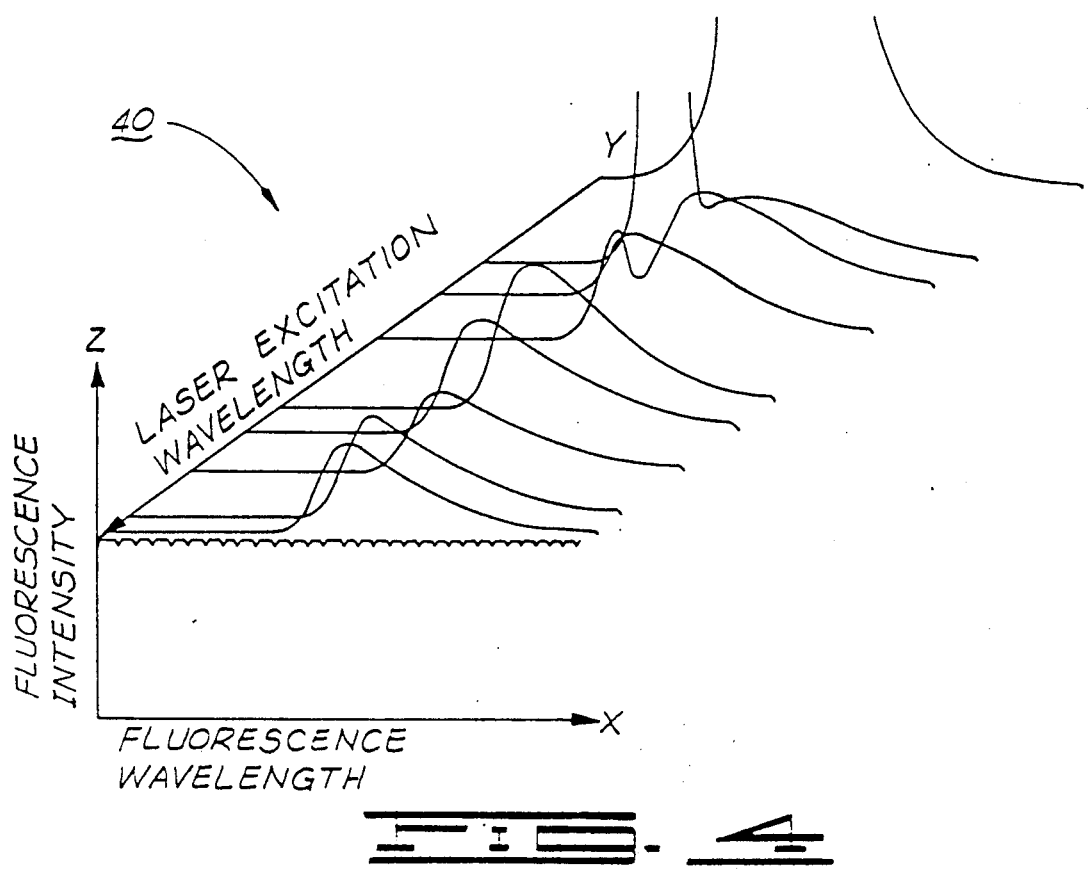
FIG. 4 is a graphic depiction of a three-dimensional spectrum of crude oil as developed by the system.

FIG. 4 shows the 3-D fluorescence spectra plot 40 of a sample of bulk crude oil taken from the same region from which the fluid inclusion thin section was obtained. A comparison of the two contours of plots 38 and 40 (FIGS. 3 and 4) indicates a correlation coefficient of 0.94, indicating that the oil in the fluid inclusion (plot 38) was the same as the crude oil (plot 40). This implies historically that the crude oil migrated through the region where the fluid inclusion sample was obtained.

Figure 5:
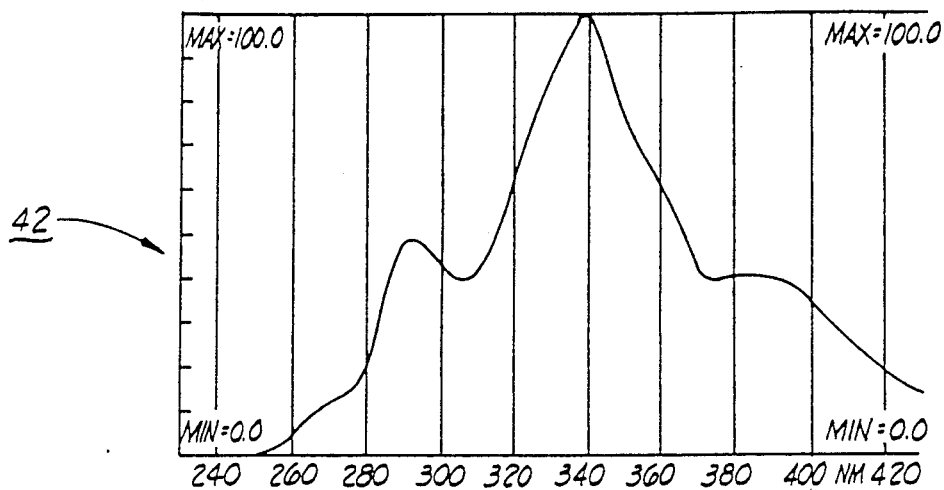
FIG. 5 is a graphic depiction of a synchronous fluorescence spectra of a very immature oil.
Figure 6:
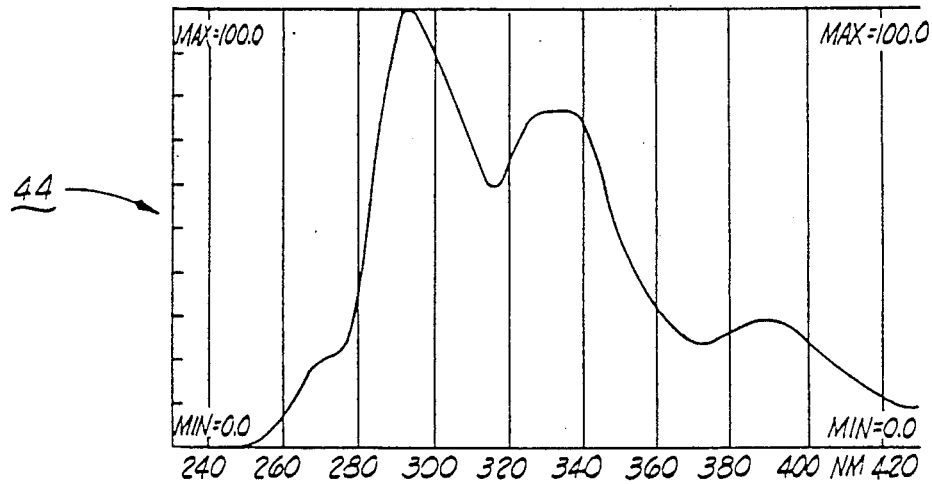
FIG. 6 is a graphic depiction of a synchronous fluorescence spectra of a moderately mature oil.
Figure 7:
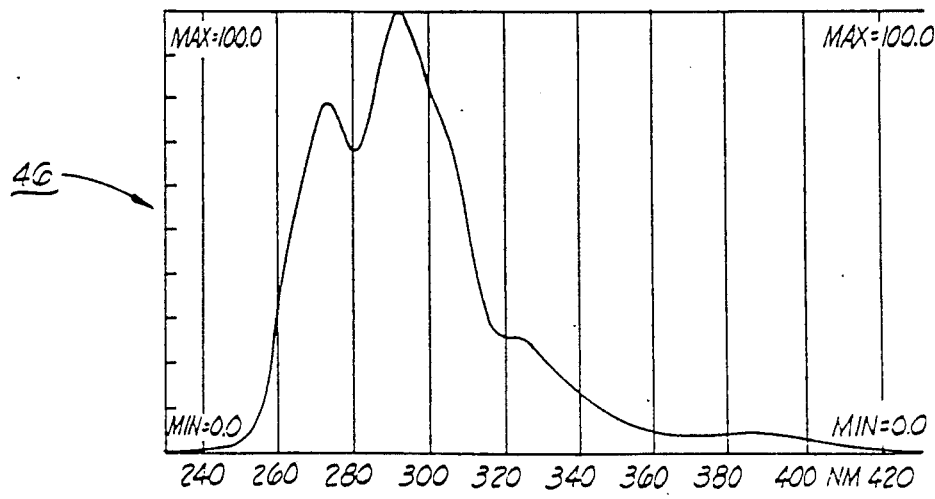
FIG. 7 is a graphic depiction of a synchronous fluorescence spectra of a condensate oil as developed by the present invention.

As a general rule, it may be noted that the fluorescence peak will shift toward shorter wavelengths as the oil matures. This was tested on bulk crude oil samples and the peak shifting was brought out even more dramatically by plotting synchronous fluorescence spectra rather than the conventional plot. FIGS. 5, 6 and 7 show the synchronous fluorescence spectra plots 42, 44 and 46 for, respectively, very immature, moderately mature, and a condensate oil. As may be seen from the plots 42, 44 and 46, the peak energy emission wavelength shifts towards the shorter wavelength end of the spectrum for the more mature oils. The similar technique will also give the same indication with fluid inclusion plots.

The synchronous fluorescence spectra of plots 42, 44 and 46 are derived by first constructing a 3-D contour plot of the data and then effecting a 45° slice through the contour data. This operation is readily performed with existing program by the computer 32 in data acquisition system 30.

Other tunable light sources may be used in place of the tunable laser 18. For example, a Xenon lamp with high intensity, narrow-band monochromator might be utilized to provide the requisite light output. Also, such as the Perkin-Elmer Model LS-5 or MPF 66 fluorescence spectrometer could be converted to measure single fluid inclusions by adding the appropriate focusing optics with or without fiber cables and a microscope stage for positioning of the inclusion in the path of excitation light.

The spectral range that contains the most information on oil appears to be from about 230 to 500 nanometers. To reach this spectral region, it is preferred that a short wavelength, tunable laser system be used such as a mode-locked, frequency doubled YAG laser, pumped, tunable, cavity-dumped doubled dye laser, or a high intensity, narrow band output monochromator.

Still another method has been developed for examination of oils using time-resolved fluorescence spectroscopy. Applications for this method include the determination of API° of oil-stained drill cuttings and cores before a drill stem test, as well as non-destructively comparing oil in first fluid inclusions to oil in other fluid inclusions, crude oils, kerogens, and source rock extracts. This process is extremely valuable in view of the fact that it can obviate the need for drill stem tests which, in some areas of the world, can require an exorbitant monetary outlay. Thus, if the API° of the oil can be determined before the test and shows low, then the drill stem test does not have to be made. At the present time, there is no way in which the API° may be determined from such as drill cuttings, cores or the like because of the small amount of oil available.

Another application of this method is for better evaluation of the petroleum potential of a reservoir or a basin, and a method for possibly determining the migration path of a given oil when there is presently no other existing technique available; for instance, when there are no biomarkers available, when oil shows are contaminated by additives to the drilling mud, or when oil-filled fluid inclusions are the only samples available.

Oil-filled fluid inclusions have previously been compared by a destructive method which required breaking the inclusions and channeling the contents into a gas chromatograph. This technique had several drawbacks since more than one inclusion had to be broken in order to acquire enough contents for gas chromatograph measurement. The contents of a single inclusion is too small. This destructive breaking and mixing destroys the individual information contained in each inclusion and mixes the contents of the inclusions. Also, if one inclusion of a multiple has strong detection characteristics, it will dominate and suppress the characteristics of the others into the noise level.

Equipment suitable for time-resolution fluorescence spectroscopy is shown in FIG. 8. The system 50 utilizes a pulsed laser system 52 in order to obtain time-resolved fluorescence spectra from oil. The output wavelength of laser system 52 should be in the ultraviolet spectral region since that is where oil absorbs best. While any of a number of different pulsed lasers may be utilized, it is preferred to use a frequency doubled, mode-locked YAG laser synchronously pumping a tunable, frequency-doubled, cavity-dumped dye laser. This laser system 52 has output wavelengths ranging from 270 to 900 nanometers (nm), pulse widths from 1 to 10 picoseconds (1 psec = $1 \times 10^{-12}$ sec.), and pulse repetition rates from 1 to 76 megahertz.

Light pulses from a frequency doubled, mode-locked YAG laser 54 are directed into a tunable dye laser 56. The output of tunable laser 56 is then directed to a frequency doubler 58 which functions to shift a portion of the light into the ultraviolet region. The ultraviolet light beam 60 is then directed into an ultraviolet microscope 62 which irradiates the specimen or sample 64. The microscope 62 may be such as a Zeiss Model USMP 80 ultraviolet microscope, and this type of microscope is needed particularly for viewing of fluid inclusions which range in size from about 2 to about 20 microns.

The sample fluorescence with a characteristic decay is collected by a spherical mirror 66 combined with a flat mirror 68 that directs the light beam onto the input slit of a monochromator 70. One suitable form of monochromator is a model HR-320 commercially available from Instruments SA, Inc. The light passing through the monochromator 70 is then detected by a fast time-response photomultiplier tube 72 that is suitably housed in a thermal electric cooler 74. In order to collect time-resolved fluorescence spectra without deconvoluting the system detection response, the detector 72 must have a rise time ten times less than the shortest fluorescence lifetime of the sample. For oil, this amounts to 1.5 nanoseconds and this requires that the rise time of the photomultiplier detector 72 be about 150 picoseconds. A suitable form of photomultiplier tube 72 is a Model R2809U-07 microchannel plate which is commercially available from Hamamatsu Inc. This PMT has the requisite rise time of 150 picoseconds.

A data processor 76 receives output from the photomultiplier tube 72 to develop output data. Data processor 76 is a digital data analyzer having extremely fast digitizing capabilities in order to convert and store the electrical signal present on line 78. A suitable form of data processor 76 may be a type Data 6000 which is commercially available from Data Precision, Inc. The data processor 76 is capable of sampling every 10 picoseconds on repetitive wave forms that are produced by the fluorescing sample due to the fact that the laser system emits pulses at a 1 to 76 megahertz repetition rate. The fast repetition rate also helps in increasing the signal-to-noise ratio (S/N) because the S/N increases as the square root of the number of spectra being averaged. Therefore, if 1000 spectra are averaged, the S/N ratio will increase about 32 times, a significant advantage.

FIG. 9 shows a typical time-resolved fluorescence spectrum of oil that was obtained using an excitation source of 354 nanometers as fluorescence emission was detected at 450 nanometers with a 5 nanometer bandwidth. The vertical axis represents the fluorescence intensity in relative units over the 5 nanometer bandwidth. The horizontal axis represents time in nanoseconds with each box or vertical line separation equal to 10 nanoseconds. It can be seen from FIG. 9 that the time-resolved fluorescence pulse consists of a leading edge or rise time 80 and a trailing edge or decay lifetime 82 which times are indicative of an oil of certain maturity. The second, smaller peak to the right of the main peak is of no interest as it is an artifact of the photomultiplier tube used. The decay curve 82 can be seen to be about 10-11 nanoseconds in time length.

It is possible to determine a trend in fluorescence lifetime with maturity or an indication of API° of oil by using the time-resolved fluorescence spectra for a plurality of selected oils of interest. As shown in FIG. 10, a graph represents results for the time-resolved fluorescence spectra for seven oil samples with concentrations at 100 ppm in heptane. Time-resolved fluorescence spectra were collected at different emission wavelength positions for each of the seven samples. Thus, the time-resolved fluorescence spectra were found at the emission wavelengths of 400 nm, 450 nm, 500 nm, 550 nm, and 600 nm for three of the oils and fewer emission wavelengths for the remaining four oils, each with 5 nm bandwidth. The fluorescence decay lifetimes for each position of each oil sample were then determined and plotted as shown in FIG. 10. The vertical axis represents fluorescence lifetimes (decay) and the horizontal axis represents emission wavelengths.

The plot shows seven curves, each representing an oil of certain maturity and, as can be seen from the plot, the fluorescence lifetimes decrease as maturity and API° increase. This is explained because more mature oils have shorter chained molecules and their excitation tends toward shorter wavelengths, and electronic transitions at shorter wavelengths will have shorter fluorescence lifetimes. The seven oil samples used included one immature oil (IM), two moderately mature oils (MM), three very mature oils (VM) and one condensate sample (COND).

Another method for comparing time-resolved fluorescence spectra is to record the time-resolved spectra for different excitation wavelengths. Specifically, samples are excited with wavelengths from 250 to 450 nm every 10 nm and the time-resolved fluorescence spectra are recorded for each of the 20 excitation wavelengths. There then results a data set that has the same format as the 3-D fluorescence spectra data as shown in FIG. 1. It follows then that a chemometrics program (to be described) developed to determine the API° of oils using 3-D fluorescence spectra can also be used to determine API° of oils using time-resolved spectroscopy. Furthermore, one can combine the 3-D and time-resolved data sets to form a new data set that can be used to determine API° of oil.

Time-resolved fluorescence spectroscopy can also be done using photon counting and phase modulation techniques. The latter requires phase modulating the laser, which is easily done with the sychronously-pumped dye laser system described in relation to FIG. 8. Furthermore, the photomultiplier tube can be replaced with a streak camera which can collect time-resolved fluorescence spectra over the entire fluorescence range of the sample. Data can then be assembled as a spectrum of fluorescence intensity versus time versus fluorescence wavelengths to yield yet another indicator giving valid differentiation of API° of oil samples.

Another mode of oil correlation has been developed in the form of an automated data processing system under control of a chemometrics computer program. The chemometrics program was specifically developed for use in examining sets of 3-D fluorescence spectra; however, it has now been determined that the chemometrics program may be used for examination of time-resolved fluorescence data or combinations of the time-resolved data and the 3-D fluorescence spectra. The program functions to group selected oils in accordance with their maturity, and the program also has the capability of determining individual components within an oil mixture. The program has the capability of comparing 3-dimensional data sets and grouping them according to their similarities. Such automated procedure greatly facilitates the study of oil maturity in fluid inclusions as well as the determination of oil migration paths in the earth.

Figure 11:
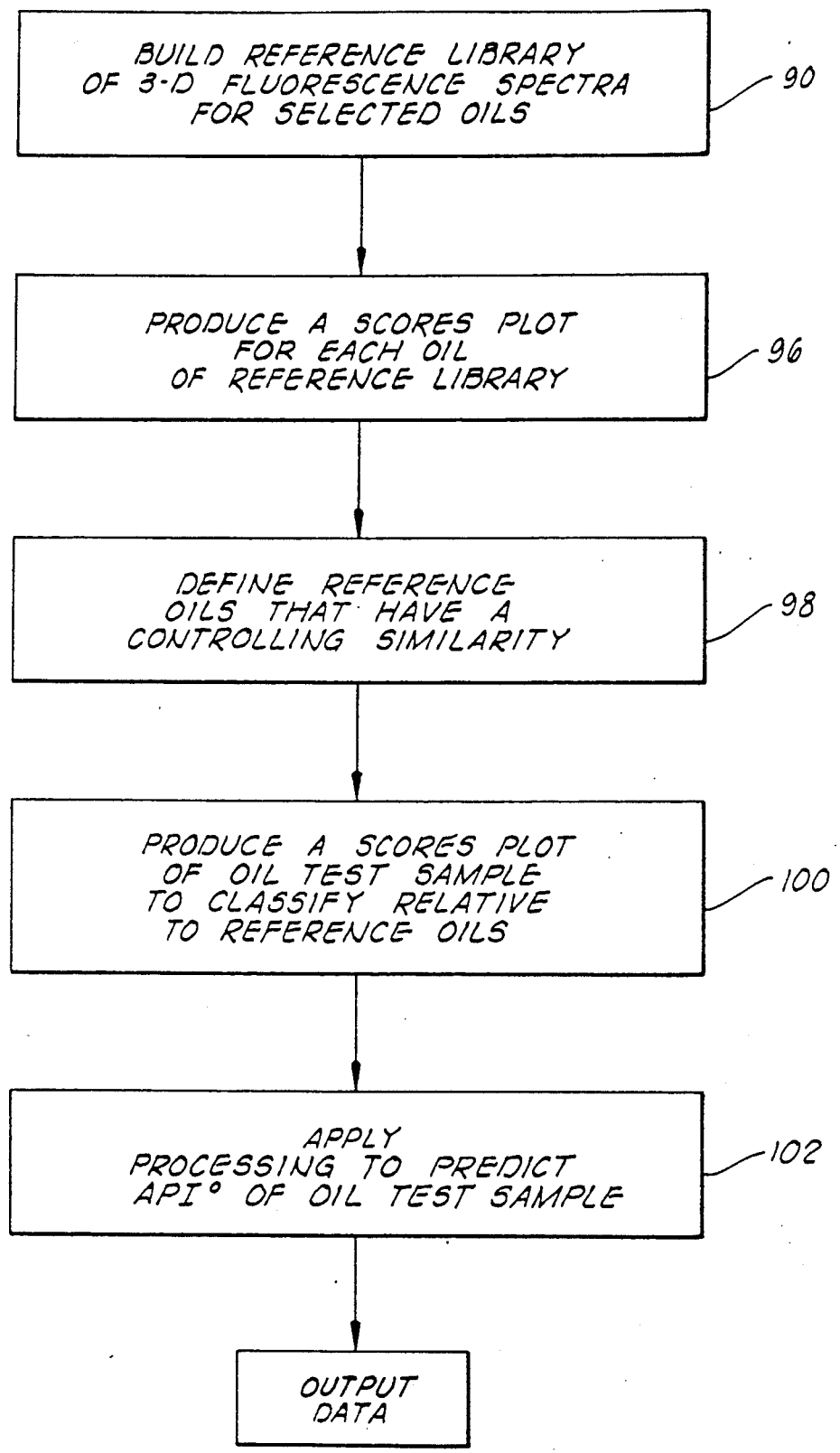
FIG. 11 is a flow diagram of a chemometrics program that functions to predict the API° gravity of an oil sample.

The chemometrics program functions to compare the 3-D fluorescence spectrum from an oil of unknown maturity to a library of 3-D fluorescence spectra derived from oils of known maturity. FIG. 11 is a generalized flow diagram of the chemometrics program, i.e., a program effective to apply mathematical, statistical and computational tools to solve problems in analytical chemistry. The program brings about a method that predicts the API° of crude oils. Flow stage 90 carries out the building of a reference library of 3-D fluorescence spectra. Thus, a group of known oils are examined to produce 3-D fluorescence spectra by using a suitable fluorescence spectrophotometer, e.g., a Perkin-Elmer MPF66, to produce 3-D fluorescence spectra for each oil sample such as that shown in FIG. 1. In the case of an oil whose presence is manifest within a fluid inclusion, a suitable microspectrophotometer such as that shown in FIGS. 2 and 8 may be utilized. An example of oils used to produce a reference library is shown in the following table listing five oil test samples.

TABLE 1

| | GEOCHEMICAL DATA ON TEST SAMPLES | | | | |
|---|---|---|---|---|---|
| SAMPLE | API° | SAT/AROM | HC/NON-HC | $<C_{15}$ | MATURITY LEVEL |
| A | — | 1.88 | 6.69 | — | early maturity |
| B | 35.8 | 3.47 | 14.4 | — | early to moderate maturity |
| C | 26.2 | 0.98 | 3.98 | — | early to moderate maturity |
| D | 40.3 | 2.38 | 13.1 | 12 | mature/very mature |
| E | 41.1 | 2.50 | 16.9 | 32 | mature |

Figure 12:
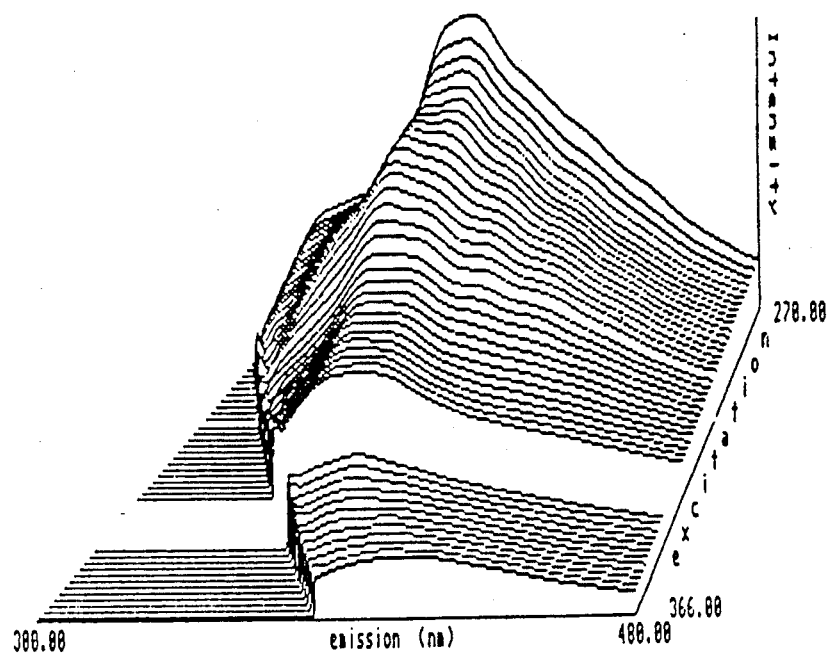
FIG. 12 is a 3-D fluorescence spectrum for a particular immature oil sample.
Figure 13:
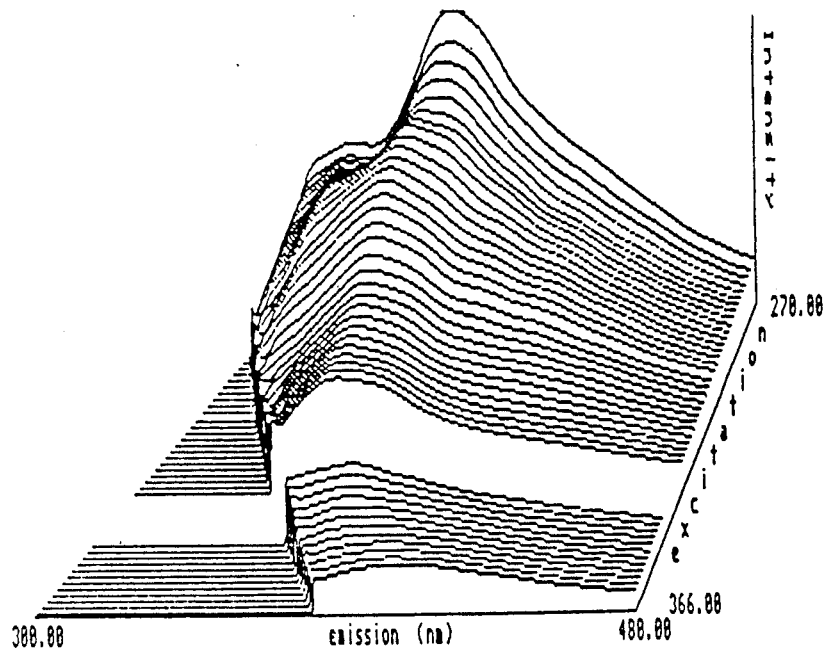
FIG. 13 is a 3-D fluorescence spectrum for a particular mature oil sample.
Figure 14:
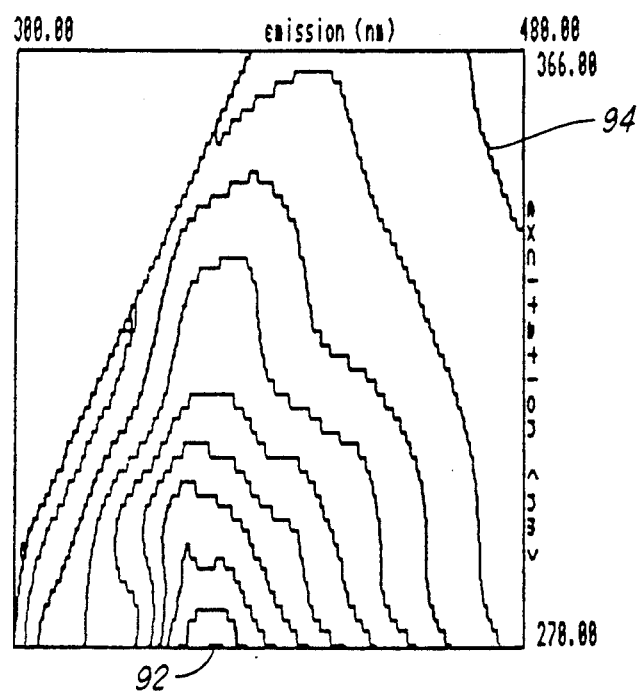
FIG. 14 is a contour fluorescence plot of the spectrum of FIG. 12.
Figure 15:
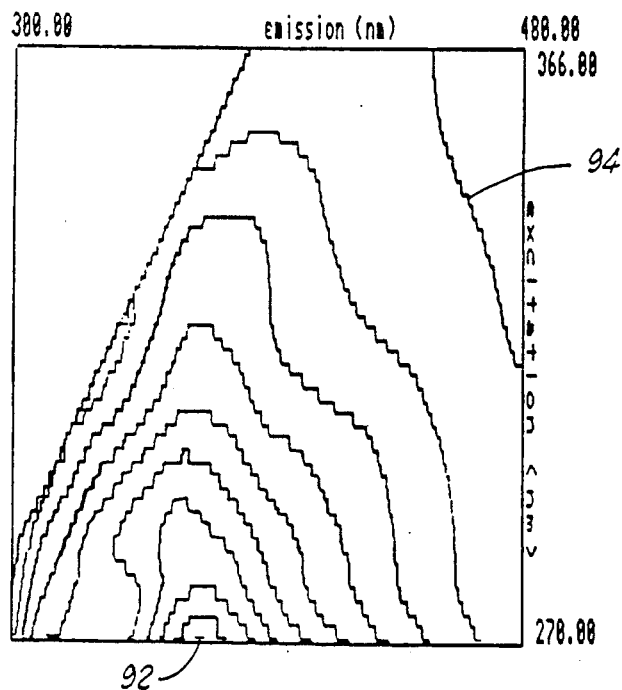
FIG. 15 is a contour fluorescence plot of the spectrum of FIG. 13.

FIGS. 12 and 13 show the 3-D fluorescence spectra for oil samples A and E, respectively. The samples B, C and D are omitted since they are similar to the spectra of samples A and E with shifting of the 3-D surface in accordance with the trend differences. FIGS. 14 and 15 illustrate the respective contour plots for each of samples A (immature) and sample E (mature). The contour plots are made at 10% of threshold value with line 92 being the 100% isobar and line 94 being the 10% isobar. Here again, the contour plot for samples B through sample D are omitted to avoid repetition.

Referring again to FIG. 11, a next flow stage 96 of the chemometric program functions to make a scores plot for each oil in the reference library. Thus, in accordance with pre-selected comparison criteria, the program effects a point-by-point analysis of the 3-D fluorescence spectrum and/or the contour plot thereof to define significant variances as between the several reference oils. The next flow stage 98 then functions to give particular identity to any detected variances as well as to group the reference oils into clusters or sub-groups having similar sub-sets of variance. For example, the following table lists a selected group of reference oils used in one particular library.

TABLE 2

| Oil No. | Area | Migration Age | Source Age | Measured API° |
|---|---|---|---|---|
| 1 | Dubai | Oligocene? | Cretaceous | 39.6 |
| 2 | Alabama | — | — | 57.2 |
| 3 | Storrington, England | Cretaceous | Jurassic | 44.6 |
| 4 | Indonesia | — | — | 47.3 |
| 5 | Norway | — | Jurassic? | 24.9 |
| 6 | Matagorda | — | — | 51.8 |
| 7 | Cat Canyon | — | — | 10.8 |
| 8 | Stockbridge 1, England | Cretaceous | Jurassic | 37.5 |
| 9 | North Sea, U.K. | — | Upper Jurassic | 35.0 |
| 10 | North Sea, U.K. | — | Upper Jurassic | 34.5 |
| 11 | North Sea, U.K. | — | Upper Jurassic | 36.6 |
| 12 | Colorado | — | — | 27.0 |
| 13 | North Sea, U.K. | — | Upper Jurassic | 33.9 |
| 14 | Ecuador | — | — | 31.2 |
| 15 | Pt. Conception, CA | — | — | 29.6 |
| 16 | Santa Maria Basin, CA | — | — | 7.94 |
| 17 | Ecuador | — | — | 21.4 |
| 18 | Ecuador | — | — | 25.2 |
| 19 | North Sea, Norway | — | — | 30.7 |
| 20 | Ecuador | — | — | 19.4 |
| 21 | Ecuador | — | — | 15.30 |
| 22 | Ecuador | — | — | 11.1 |
| 23 | Ecuador | — | — | 11.1 |

Figure 16:
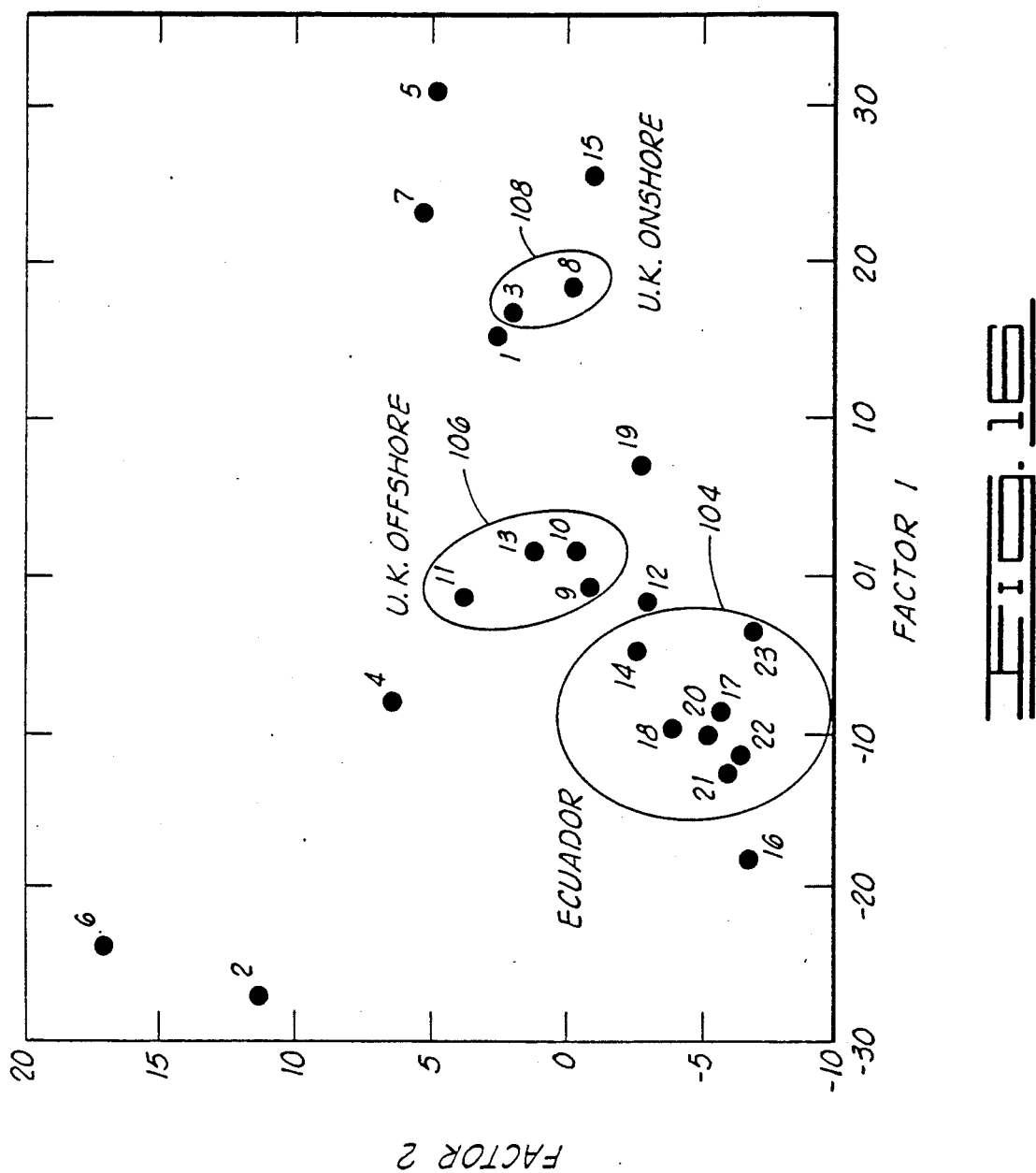
FIG. 16 is a scores plot derived from the chemometrics program.

Flow stage 100 produces and classifies a scores plot of each reference oil and stage 102 compiles the API° related data. FIG. 16 shows a scores plot compiled by the chemometrics program relative to those reference library oils listed in Table 2. A plot of factors 1 and 2 derived by the chemometrics program are established in the scores plot and the oil sample ID numbers from Table 2 are indicated next to each plot point of FIG. 16. Distinct clusters or subgroups 104, 106 and 108 are delineated since they have distinct similarities. Outlying points are disregarded to increase accuracy and predictions are made in this case within plus or minus 2 API° accuracy. The prediction accuracy relative to the Ecuador oils, cluster 104, is illustrated in the following table.

| ID# | PREDICTED API | MEASURED API |
| --- | --- | --- |
| 14 | 32.8 | 31.2 |
| 17 | 21.0 | 21.4 |
| 18 | 24.9 | 25.2 |
| 20 | 16.4 | 19.4 |
| 21 | 15.4 | 15.3 |
| 22 | 13.8 | 11.1 |
| 23 | 10.1 | 11.1 |

And, the prediction accuracy for all 23 oils of Table 2, taken collectively, are as follows:

| ID# | PREDICTED API | MEASURED API |
| --- | --- | --- |
| 1 | 32.0 | 39.6 |
| 2 | 49.6 | 57.2 |
| 3 | 29.2 | 44.6 |
| 4 | 36.5 | 47.3 |
| 5 | 38.2 | 24.9 |
| 6 | 57.0 | 51.8 |
| 7 | 38.1 | 10.8 |
| 8 | 21.7 | 37.5 |
| 9 | 30.1 | 35.0 |
| 10 | 31.1 | 34.5 |
| 11 | 37.4 | 36.6 |
| 12 | 29.2 | 27.0 |
| 13 | 35.0 | 33.9 |
| 14 | 28.4 | 31.2 |
| 15 | 31.6 | 29.6 |
| 16 | 25.6 | 7.49 |
| 17 | 20.5 | 21.4 |
| 18 | 24.1 | 25.2 |
| 19 | 21.9 | 30.7 |
| 20 | 18.8 | 19.4 |
| 21 | 18.8 | 15.3 |
| 22 | 17.3 | 11.1 |
| 23 | 15.5 | 11.1 |

So the first version of the chemometrics program indicates that the oils should first be clustered as at 104, 106 and 108 in FIG. 16, then API° is estimated to increase accuracy of prediction. Further refinement in the program showed a plus or minus 2 API or better for a library of forty-nine oils.

Figure 17:
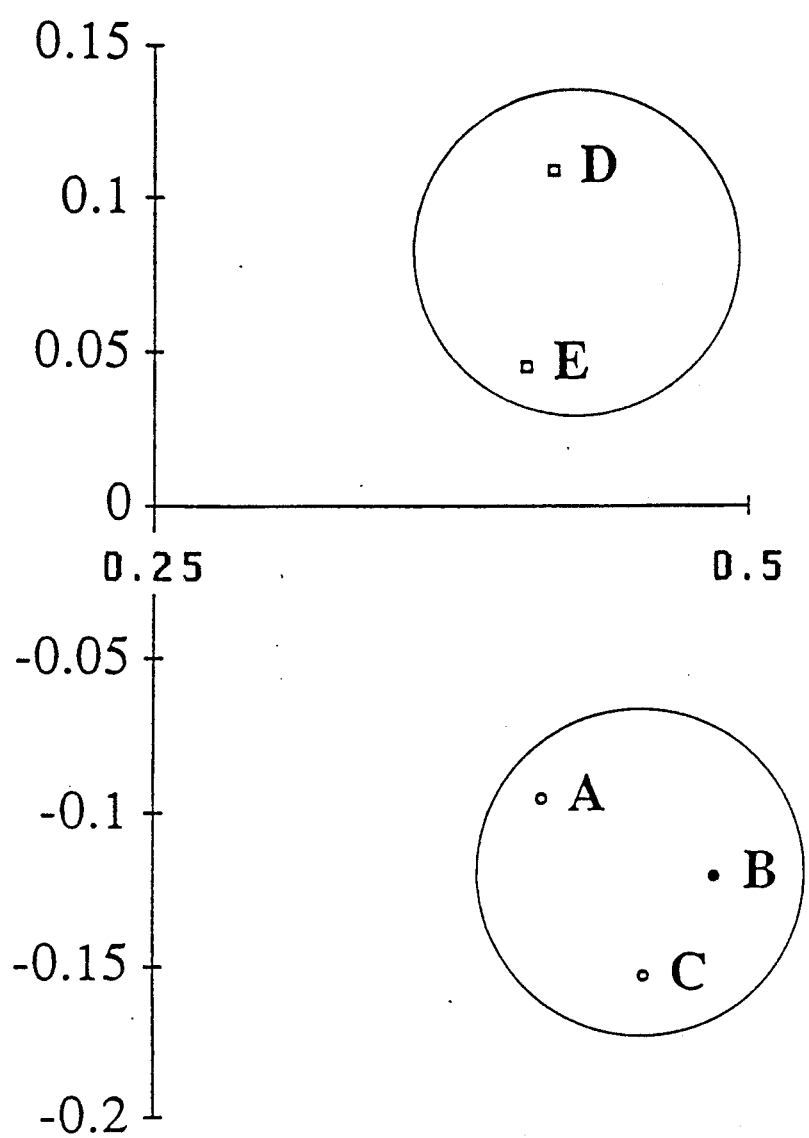
FIG. 17 is a maximum variance projection for five oil samples to illustrate grouping.

The 3-D fluorescence spectra for the five oil samples A-E of Table 1 were collected on a Perkin-Elmer Model LS-4 fluorescence spectrometer. The oil samples were dissolved 100 ppm in hexane. The spectrometer was controlled to collect one fluorescence spectrum (2-D) for each excitation wavelength. That is, excitation wavelengths were stepped every two nanometers from 270 to 366 nm giving a total of 49 fluorescence spectra per 3-D plot. The 49 fluorescence spectra were laid side by side to produce 3-D plots A through E as shown for example in FIGS. 12 and 13, the samples A and E spectra, respectively. The wavelength range of fluorescence was from 300 to 480 nanometers. The input and output slits on the LS-4 spectrometer were adjusted to give spectral bandwidth of 10 nm for the excitation wavelengths and 5 nm spectral resolution for the fluorescence spectra. FIG. 17 shows the results of the test. The chemometrics program grouped all of the oils correctly; that is, the immature oils A, B and C grouped together and the mature oils D and E grouped together.

The chemometrics program has been implemented on a VAX computer, Digital Equipment Corp. The fluorescence spectra were collected on a MPF66 Fluorescence Spectrophotometer controlled by a Perkin-Elmer Model 7500 computer. The collected fluorescence data was placed in a Perkin-Elmer format in the 7500 computer. A conversion program (CONVERT), supplied by Perkin-Elmer, was installed which then processed the spectral data into seven bit ASCII data files. These ASCII data files were then transferred via a 1200 Baud telephone modem to an IBM AT computer running a blind ASCII data capture routine (PIBTERM). Transferred files are then named according to the sample ID number supplied, and superfluous header and trailer information may be stripped from each file. Finally, the processed ASCII files were transferred to Model PDP 11/44 disc files (Digital Equipment Corp.) via a serial link between the IBM PC and the DEC 11/44 using the "KERMIT" transfer protocol. A magnetic tape prepared on the RSX system is a standard files-11 volume using standard "initialize", "mount", and "PIP" commands. The magnetic tape is directly readable on the VAX computer using a readily available mount command syntax.

A modified version of the system allows for similar transfers of data in much simplified manner. Thus, transfer of data is carried out by: (1) integrating the conversion of spectral data to ASCII directly into the data acquisition and storage procedure via an OBEY program; (2) using a disc conversion program to convert to an IBM PC or DEC readable format, or; (3) the implementation of a file transfer protocol on the Perkin-Elmer 7500 that is coupled to a direct serial line link to the VAX computer (DEC).

FIG. 18 illustrates a micro 3-D fluorescence system, that has evolved for use in micro-detection of fluorescence spectra of oil-carrying substances. The system 120 produces 3-D fluorescence spectra with high resolution and excellent signal-to-noise ratios. Resolution on the order of 0.12 Angstrom and signal-to-noise ratios upwards of 250 are possible. The use of the chemometrics software package can then be employed to best advantage in examining spectra derived by system 120.

The system 120 consists of a xenon lamp 122 providing ultraviolet illuminaton to an excitation monochromator 124 that provides an output beam 126 to a light chopper 128. The excitation monochromator 124 functions to provide continuously tunable light for illuminating the sample under the microscope. Light in the range of 200 nm to 40 microns is available. An optical feedback sensor 130 provides reference input to a feedback controller 132 for control adjustment of the lamp power supply 134 in order to reduce fluctuations in light output. The optical feedback system maintains the output light levels to within 0.01% by adjusting the current driving the lamp 122. The excitation monochrometer 124 is also controlled by scan controller 136 receiving clock input via line 138 from the computer 140, as will be further described.

Output light beam 126 from monochromator 124 is chopped by a mechanical chopper 128 at a repetition rate of 400 hertz and a 50% duty cycle. Light leaving the chopper 128 is, therefore, a 400 hertz squarewave that is "ON" half the time and "OFF" half the time. A chopper controller 142 locks the chopper to 400 hertz while also providing a reference signal via line 144 to lock-in amplifiers 146 and 148, to be further discussed. Chopped light beam 150 is collimated by a series of cylindrical lenses 152 and 154, and about 8% of the light is tapped off by a beam splitter 156 and directed onto a photodiode sensor 158. Sensor 158 is used to compensate for any fluctuations in light output intensity from the monochromator 124 as a transimpedence amplifier 160 converts the current output of the sensor 158 into a reference voltage for input to control lock-in amplifiers 146 and 148.

The light beam 164 passing through the beam splitter 156 enters an ultraviolet microscope 166 which focuses the light onto the selected sample. A suitable form of microscope for collection of fluorescence spectra from microsamples in the deep ultraviolet region is the Zeiss USMP 80. When the sample is irradiated in UV microscope 166, it fluoresces and the fluorescence emission is directed onto the input slit of a detection monochromator 168 by means of a spherical mirror 170 and a flat mirror 172. This configuration is similar to that depicted in FIG. 8.

A photomutiplier tube 174 continuously controlled within a thermo-electrically cooled housing 176 converts a detected light beam 178 into a time analog electrical signal on lead 180. It is the electrical signal as a function of wavelength that represents the fluorescence spectrum of the sample. A power supply 182 provides power to the thermoelectric cooler 176 and the photomultiplier tube 174 is biased under control applied on lead 184 as will be further described. Output on lead 180 is then applied to the input channel of lock-in amplifier 148 which functions in concert with lock-in amplifier 146 to provide synchronous detection and source compensation.

In order to compensate for source fluctuations, the output of lock-in amplifier 146 is fed to the ratio input of lock-in amplifier 148. Reference signals of the 400 hertz input light on lead 144 are fed into both lock-in input channels of the lock-in amplifiers 146 and 148. The lock-in amplifier 148 source compensates by dividing the fluorescence signal that it detects by the output on lead 186 from lock-in amplifier 146. Such ratioed output on lead 188 is fed into the analog input of bias and scanning control 190, known commercially as a Spectra-Link electronics package, available from Instruments SA, Inc. This electronics package also biases the photomultiplier tube 174 via lead 184 and controls the scanning of monochromator 168 by the output 192. The bias and scanning control stage 190 also digitizes the ratioed signal from lock-in amplifier 148 and provides digital output on lead 194 for input to a computer 140, an IBM Model AT. The computer 140 provides output via line 138 to control each of the scanning control 190, lock-in amplifiers 146 and 148, scan controller 136, visual output monitor 196, and plotter 198. The IBM AT manipulates, displays and stores spectra and controls the detection monochromator 168 through scanning control 190 with built-in software routines.

The foregoing discloses systems and data processing techniques enabling prediction of physical properties of selected samples based upon other known properties of the sample, a process type calibration. Such procedure finds value in situations where certain physical properties suitable for prediction are readily available and inexpensive to obtain. Computational techniques enable data modeling through regression methods such as multiple linear regression in order to estimate parameters of the model. Such model construction plus other soft modeling methods, e.g., partial least squares, or principal component regression, can also be applied in refining the prediction. The prediction of API° and maturity of oil from the fluorescence emission-excitation matrix of samples is the type of problem appropriate for such modeling techniques.

The present analysis method is capable of finding 3-D surfaces, using UV excitation and fluorescence emission, that describe oils of different maturities and different API°. In addition, the system can compile what are termed 4-D surfaces using a combination of excitation, fluorescence and determination of fluorescence decay lifetimes, these too describing different maturities and different API° factors. In essence, the result of the described techniques enable the automated determination of oil quality factors for a number of oil-containing liquids, cuttings, source rock extracts, kerogens, fluid inclusions and the like.

The foregoing discloses a novel form of optical source/detector combination for use in identifying components in a multi-component mixture. More particularly, the device is capable of microscopic imaging of oil-filled fluid inclusions as derived from a particular site of interest for derivation of characteristic spectral plots identifying particular oils or hydrocarbon products of singular nature to enable positive in situ allocation. With this tool it is possible to identify more precisely the types of oils and respective migration paths through geologic time while avoiding the ambiguity and uncertanties that develop when using crushed or mixed earth samples. While the API parameter has been stressed because it is a significant factor in the art, there may be other components or compounds that are critical in correlation of oils to indicate quality, similarities, reservoir communication and the like.

Changes may be made in combination and arrangement of elements as heretofore set forth in the specification and shown in the drawings; it being understood that changes may be made in the embodiments disclosed without departing from the spirit and scope of the invention as defined in the following claims.

The embodiments of the invention in which an exclusive property or privilege is claimed are defined as follows:

1. A method for determining the quality of one or more selected oils, comprising:
   collecting 3-D fluorescence spectra for a plurality of reference oils having known maturities;
   processing the 3-D fluorescence spectra and the contour plot of each oil to produce a scores plot and compiling a reference library of scores plot data;
   dividing the scores plots for the plurality of oils into plural subgroups by classifying in accordance with predetermined similarity criteria;
   producing a sample scores plot for the 3-D. fluorescence spectra of a selected sample oil; and
   defining the sub-group within which the sample scores plot falls and, on the basis of the scores plots for the sub-group, forming a prediction model to predict the maturity of the sample oil.

2. A method as set forth in claim 1 wherein: the maturity is indicated in units of API° gravity.

3. A method as set forth in claim 1 wherein: said sample oil is crude oil.

4. A method as set forth in claim 1 wherein said sample oil is a fluid inclusion.

5. A method as set forth in claim 1 wherein: said sample oil is a source rock extract.

6. A method as set forth in claim 1 wherein: said sample oil is a kerogen.

7. A method as set forth in claim 1 wherein: said sample oil is from oil-stained drill cuttings.

8. A method as set forth in claim 1 where said step of defining further includes: predicting the gravity of the sample oil in API°.

9. A method as set forth in claim 1 where said step of defining further includes: predicting the ratio of saturates to aromatics for the sample oil.

10. A method as set forth in claim 1 where said step of defining further includes: predicting the ratio of hydrocarbons to non-hydrocarbons for the sample oil.

11. A method as set forth in 1 wherein said step of collecting 3-D fluorescence spectra is further characterized in that: the API° gravity is known for each of the reference oils.

12. A method as set forth in claim 1 wherein: the migration age and source age are defined for each of the reference oils.

13. A method as set forth in claim 1 wherein said step of collecting 3-D fluorescence spectra is further characterized in that: the ratio of saturates to aromatics is known for each of the reference oils.

14. A method as set forth in claim 1 wherein said step of collecting 3-D fluorescence spectra is further characterized in that: the ratio of hydrocarbons to non-hydrocarbons is known for each of the reference oils.

* * * * *